(12) United States Patent
Mehta

(10) Patent No.: US 8,845,972 B2
(45) Date of Patent: *Sep. 30, 2014

(54) PROCESS AND APPARATUS FOR EFFICIENT RECOVERY OF DICHLOROHYDRINS

(71) Applicant: Dow Global Technologies LLC, Midland, MI (US)

(72) Inventor: Anil Mehta, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/900,773

(22) Filed: May 23, 2013

(65) Prior Publication Data

US 2013/0259766 A1 Oct. 3, 2013

Related U.S. Application Data

(62) Division of application No. 12/935,299, filed as application No. PCT/US2009/037486 on Mar. 18, 2009, now Pat. No. 8,471,077.

(60) Provisional application No. 61/043,583, filed on Apr. 9, 2008.

(51) Int. Cl.
| | |
|---|---|
| *B01J 19/00* | (2006.01) |
| *C07C 29/82* | (2006.01) |
| *B01J 8/00* | (2006.01) |
| *B01J 19/24* | (2006.01) |
| *B01D 3/00* | (2006.01) |
| *B01D 3/10* | (2006.01) |
| *B01D 3/14* | (2006.01) |
| *C07C 17/00* | (2006.01) |
| *C07C 31/34* | (2006.01) |

(52) U.S. Cl.
CPC .................. *B01J 19/00* (2013.01); *C07C 29/82* (2013.01); *B01D 3/143* (2013.01)
USPC ........... 422/129; 422/187; 422/198; 422/600; 422/630; 422/631; 549/512; 549/513; 549/514; 568/840; 568/841; 568/844

(58) Field of Classification Search
CPC .......... B01D 1/00; B01D 23/00; B01D 3/009; B01D 3/00; B01D 3/10; B01D 3/14; B01J 19/0093; B01J 2219/00006; B01J 8/0285; B01J 27/188; B01J 19/00; B01J 19/0013; B01J 19/24; B01J 8/00; B01J 7/00; B01J 2219/00094; B01J 8/02; B01J 8/08; B01J 8/18; B01J 2219/00; B01J 19/00002; B01J 19/00027; B01J 19/00038; B01J 19/004; C07C 29/149; C07C 33/02; C07C 29/62; C07C 31/34; C07C 29/80; C07C 17/00; C07C 31/00; C07D 321/00; C07D 303/04; C07D 303/48; C07D 303/36
USPC .......... 422/129, 187, 198; 549/200, 512–514; 568/300, 700, 840, 841, 844, 913
See application file for complete search history.

(56) References Cited

U.S. PATENT DOCUMENTS

| | | | | |
|---|---|---|---|---|
| 4,783,242 | A | * | 11/1988 | Robbins .......................... 203/87 |
| 5,227,541 | A | | 7/1993 | Mori et al. |
| 5,486,627 | A | * | 1/1996 | Quarderer et al. ............ 549/521 |
| 8,591,766 | B2 | * | 11/2013 | Gilbeau ................... 252/182.12 |
| 2013/0202497 | A1 | * | 8/2013 | Tirtowidjojo et al. ........ 422/187 |

FOREIGN PATENT DOCUMENTS

| | | | |
|---|---|---|---|
| CN | 101007751 | A * | 8/2007 |
| EP | 1752435 | | 2/2007 |
| EP | 1762556 | | 3/2007 |
| WO | 2005021476 | | 3/2005 |
| WO | WO 2005/054167 | A1 * | 6/2005 |
| WO | 2006020234 | | 2/2006 |
| WO | WO 2006/106154 | A1 * | 10/2006 |

OTHER PUBLICATIONS

Machine translation of CN101007751A, which was published Aug. 1, 2007.*

* cited by examiner

*Primary Examiner* — Natasha Young

(57) ABSTRACT

A process and apparatus is disclosed for recovering dichlorohydrins from a hydrochlorination reactor effluent stream comprising dichlorohydrins, one or more compounds selected from esters of dichlorohydrins, monochlorohydrins and/or esters thereof, and multihydroxylated-aliphatic hydrocarbon compounds and/or esters thereof, and optionally one or more substances comprising water, chlorinating agents, catalysts and/or esters of catalysts. The reactor effluent stream is distilled to produce a dichlorohydrin-rich vapor phase effluent stream. The dichlorohydrin-rich vapor phase effluent stream is cooled and condensed in two unit operations conducted at two different temperatures and a portion of the liquid phase effluent stream produced by the first unit operation is recycled to the distillation step for reflux. Product streams produced by the process and apparatus are suitable for further processing in a further unit operation, such as dehydrochlorination. Advantages include recovery of high purity dichlorohydrins, more efficient recovery of dichlorohydrins, and reduced capital investment in the recovery equipment.

6 Claims, 2 Drawing Sheets

PROCESS AND APPARATUS FOR EFFICIENT RECOVERY OF DICHLOROHYDRINS

BACKGROUND OF THE INVENTION

The present invention relates to processes and apparatus for recovering dichlorohydrins from a mixture comprising the same such as the effluent generated by a process for converting multihydroxylated-aliphatic hydrocarbon compound(s) and/or ester(s) thereof to chlorohydrins.

Dichlorohydrins are useful in preparing epoxides such as epichlorohydrin. Epichlorohydrin is a widely used precursor to epoxy resins. Epichlorohydrin is a monomer which is commonly used for the alkylation of para-bisphenol A. The resultant diepoxide, either as a free monomer or oligomeric diepoxide, may be advanced to high molecular weight resins which are used for example in electrical laminates, can coatings, automotive topcoats and clearcoats.

Glycerin is considered to be a low-cost, renewable feedstock that is a co-product of the biodiesel process for making fuel. It is known that other renewable feedstocks such as fructose, glucose and sorbitol can be hydrogenolized to produce mixtures of vicinal diols and triols, such as glycerin, ethylene glycol, 1,2-propylene glycol, 1,3-propylene glycol and the like. With abundant and low cost glycerin or mixed glycols, economically attractive processes for recovering dichlorohydrins from effluents produced by the above processes are desired.

A process is known for the conversion of glycerol (also referred to herein as "glycerin") to mixtures of dichloropropanols, compounds I and II, as shown in Scheme 1below. The reaction is carried out in the presence of anhydrous HCl and an acetic acid (HOAc) catalyst with water removal. Compounds I and II can then be converted to epichlorohydrin via treatment with caustic or lime.

Scheme 1: Hydrochlorination of Glycerol

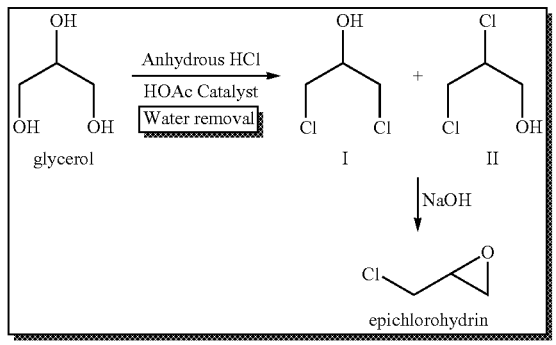

Various processes using the above chemistry in Scheme 1 have been reported in the prior art. For example, epichlorohydrin can be prepared by reacting a dichloropropanol such as 2,3-dichloro-1-propanol or 1,3-dichloro-2-propanol with base. Dichloropropanol, in turn, can be prepared at atmospheric pressure from glycerol, anhydrous hydrochloric acid, and an acid catalyst. A large excess of hydrogen chloride (HCl) was recommended to promote the azeotropic removal of water that is formed during the course of the reaction.

WO 2006/020234 A1 describes a process for conversion of glycerol or an ester or a mixture thereof to a chlorohydrin, comprising the step of contacting a multihydroxylated-aliphatic hydrocarbon compound, an ester of a multihydroxylated-aliphatic hydrocarbon, or a mixture thereof with a source of a superatmospheric partial pressure of hydrogen chloride to produce chlorohydrins, esters of chlorohydrins, or mixtures thereof in the presence of an organic acid catalyst. This process is referred to herein as a "dry process" because the process uses dry hydrogen chloride and the source of water in the process is essentially only the water generated as a co-product in the reaction. In the dry process, azeotropic removal of water, via a large excess of hydrogen chloride, is not required to obtain high chlorohydrins yield. WO 2006/020234 A1 further teaches that separation of the product stream from the reaction mixture may be carried out with a suitable separation vessel such as one or more distillation columns, flash vessels or extraction columns WO 2006/020234 A1 does not describe a specific process and apparatus for efficient recovery of dichlorohydrins.

WO 2005/021476 A1 describes a process using atmospheric partial pressure of hydrogen chloride, acetic acid as the catalyst, and a cascade of loops, preferably three loops, each loop consisting of a reactor and a distillation column in which water of reaction, residual hydrogen chloride and dichloropropanol are removed from the reaction effluent. This process for reaction and distillation requiring a cascade of reactor/distillation loops is very expensive as it requires several reactor/column loops in the process. Furthermore, valuable acetic acid is lost with the distillate during distillation, resulting in a large rate of acetic acid consumption in the process, making the process expensive to operate.

EP 1 752 435 A1 (also published as WO 2005/054167) as well as EP 1 762 556 A1 disclose another process for producing a chlorohydrin by reaction between glycerol and aqueous hydrogen chloride to produce dichlorohydrins. The process disclosed in EP 1 752 435 A1 and EP 1 762 556 A1 is referred to herein as a "wet process" because the process not only produces water from the reaction but also adds a large amount of water into the process via the aqueous hydrogen chloride reactant. The wet process described in the above prior art requires three separation columns; a distillation column for distillation of the reactor's gas phase to remove the large excess of water from the reaction medium while keeping hydrogen chloride in the process; a stripper column to strip water and hydrogen chloride from the reactor's liquid phase; and yet another distillation or a stripping column for recovering dichloropropanol from the liquid phase exiting the stripper. Some dichloropropanol is removed from the reaction medium in the first and the second separation columns because of existence of a pseudoazeotrope among dichloropropanol, water and hydrogen chloride. The main fraction of dichloropropanol is collected from the top of the distillation or stripping column, the third separation column. The column residue is recycled to the reactor. This process has very high energy consumption because of the need to evaporate a large amount of water from the process. This process is unsuitable for efficiently recovering dichlorohydrins from a reaction effluent of a dry process.

CN 101007751A describes another process that combines wet and dry processes with two reactors in series, in which a tubular reactor is used as the first reactor and a foaming-tank reactor is used as the second reactor. Aqueous hydrogen chloride is fed to the tubular reactor and gaseous hydrogen chloride is fed to the foaming-tank reactor. Inert impurities are added to the hydrogen chloride in order to improve efficiency of stripping water from the reaction mixture in the foaming-tank reactor. This process requires much greater use of HCl than that required for reaction and dichlorohydrin yield is relatively low.

Opportunities remain to further improve recovery of dichlorohydrins, from a dichlorohydrins comprising stream, in a form that can be used in subsequent conversions, such as the conversion to epichlorohydrin. Accordingly, it is desired to provide improved processes and apparatus with specific steps for separating the product dichlorohydrin from the reaction effluent of hydrochlorination of multi-hydroxylated aliphatic hydrocarbon compounds. It is also desired provide a significant reduction in capital and operating cost of a process for recovering dichlorohydrins which can be integrated into a glycerine hydrochlorination process as well as glycerine to epichlorohydrin process. It is further desired to provide a process that uses only one distillation column to recover dichlorohydrins from a dichlorohydrins comprising stream and can provide a high purity dichlorohydrin stream.

SUMMARY OF THE INVENTION

The present invention provides the desired process for improved recovery of dichlorohydrins, from a dichlorohydrins comprising stream that does not have the disadvantages of the prior art processes.

One aspect of the present invention is a process for recovering dichlorohydrin(s) from a mixture comprising dichlorohydrin(s), water, one or more compounds selected from monochlorohydrin(s), ester(s) of chlorohydrin(s), and multi-hydroxylated-aliphatic hydrocarbon compound(s) and/or ester(s) thereof, and, optionally, one or more substances comprising chlorinating agent(s), catalyst(s), ester(s) of catalyst(s), and/or heavy byproducts, wherein the process comprises:
  (a) distilling or fractionating the mixture under reflux conditions to separate from the mixture a first vapor phase effluent stream having a first temperature and comprising at least dichlorohydrin(s) and water;
  (b) cooling the first vapor phase effluent stream of step (a) nonadiabatically to a second temperature lower than the first temperature of step (a) to condense a fraction of the first vapor phase effluent stream of step (a) to produce a first condensed liquid-phase effluent stream and a second vapor phase effluent stream having the second temperature;
  (c) separating the first condensed liquid-phase stream of step (b) into a first fraction and a second fraction;
  (d) recycling the first fraction of step (c) to step (a) as reflux for step (a); and
  (e) cooling the second vapor phase effluent stream of step (b) nonadiabatically to a third temperature lower than the second temperature of the second vapor phase effluent stream to condense at least a fraction of the second vapor phase effluent stream of step (b) to produce a second condensed liquid-phase effluent stream and, optionally, a third vapor phase effluent stream having the third temperature, wherein the second temperature of step (b) is selected to produce a first condensed liquid-phase effluent stream containing more than 50 weight-percent dichlorohydrin.

Another aspect of the present invention is an apparatus suitable for producing dichlorohydrin(s) from multihydroxylated-aliphatic hydrocarbon compound(s) and/or ester(s) thereof comprising:
  (1) A reactor system suitable for carrying out hydrochlorination of multi-hydroxylated aliphatic hydrocarbon compound(s) and/or ester(s) thereof comprising one or more reactors connected in series or in parallel;
  (2) a separation system comprising at least one liquid-vapor contacting device (41) suitable for distillation and/or fractionation of a reactor effluent stream obtainable from the reactor system (30) and, optionally, at least one flash vessel;
  (3) a first condensation system comprising a first cooling device (51) and optionally a first reservoir (52) connected to the cooling device (51) for accumulation of condensate from the first cooling device (51); and
  (4) a second condensation system comprising a second cooling device (61) and optionally (a) a second reservoir (62) connected to the second cooling device (61) for accumulation of condensate from the second cooling device (61) and/or (b) a liquid-liquid phase separation device (66) connected to the second cooling device (61) for separating a liquid phase comprising aqueous and organic components into an aqueous phase and an organic phase separate from the aqueous phase, wherein the reactor system (30) is connected to the separation system (40) for conducting a reactor effluent stream (34) from the reactor system (30) to the separation system (40) for distillation and/or fractionation of the reactor effluent stream (34), the separation system (40) is connected to the first condensation system (50) for conducting a first vapor phase distillation and/or fractionation effluent stream (47) from the separation system (40) to the first condensation system (50), the first condensation system (50) is connected to the second condensation system (60) for conducting a second vapor phase effluent stream (57) from the first condensation system (50) to the second condensation system (60), and the first condensation system (50) is connected to the separation system (40) for conducting a fraction (54, 55) of a first condensed liquid-phase effluent stream (53) from the first condensation system (50) to the separation system (40).

BRIEF DESCRIPTION OF THE DRAWINGS

For the purpose of illustrating the present invention, the drawings show embodiments of the present invention which are presently preferred. However, it should be understood that the present invention is not limited to the precise arrangements and instrumentalities shown in the drawings. In the accompanying drawings, like reference numerals are used to denote like parts throughout the several drawings.

DETAILED DESCRIPTION OF THE INVENTION

Definitions

Figure 1:
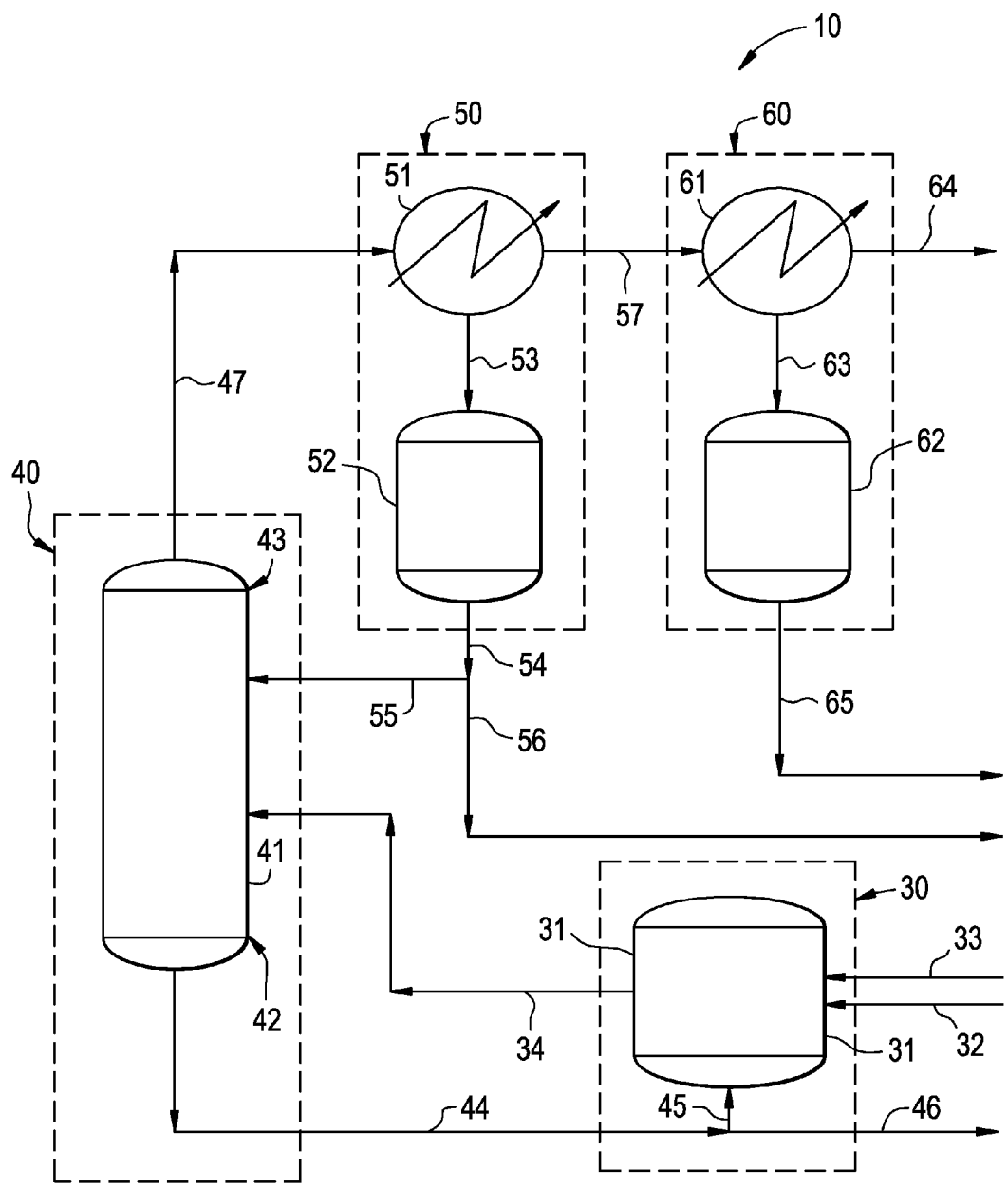
FIG. 1 is a process diagram illustrating a first embodiment of the present invention.

As used herein, the term "multihydroxylated-aliphatic hydrocarbon compound" (abbreviated hereafter as "MAHC") refers to a compound that contains at least two hydroxyl groups covalently bonded to two separate vicinal carbon atoms and no ether linking groups. They contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3- 1,4-, 1,5- and 1,6-diol functional groups as well. Geminal-diols, for example, are precluded from this class of MAHCs.

The MAHCs contain at least 2, preferably at least 3, up to about 60, preferably up to 20, more preferably up to 10, even more preferably up to 4, and yet more preferably up to 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least 2, and preferably at least 3, up to about 60, preferably up to 20, more preferably up to 10, even more preferably up to 4, and yet more preferably up to 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). Dichlorohydrins produced by hydrochlorination of glycerin or glycerin esters include 1,3-dichloro-2-propanol and 2,3-dichloro-1-propanol.

As used herein, the expression "under hydrochlorination conditions" means conditions capable of converting at least 1 wt. %, preferably at least 5 wt. %, more preferably at least 10 wt. % of MAHCs, MCHs, and esters of MAHCs and MCHs present in a mixture and/or feed stream into DCH(s) and/or ester(s) thereof.

As used herein, the term "byproduct(s)" means compound(s) that is/are not chlorohydrin(s) and/or ester(s) thereof and/or chlorinating agent(s) and that do not form chlorohydrin(s) and/or ester(s) thereof under the hydrochlorinating conditions selected according to the present invention.

The expression "heavy byproduct(s)" refer to oligomers of mixture (a) components, such as oligomers of MAHCs and/or esters thereof and oligomers of chlorohydrins and/or esters thereof, and derivatives of such oligomers, such as esters thereof, chlorinated oligomers, and/or chlorinated esters thereof, having a number average molecular weight equal to or greater than the number average molecular weight of the oligomer, such as chlorinated oligomers. The terms chlorohydrin(s), MCH(s) and DCH(s), and ester(s) thereof, are not intended to include heavy byproducts.

The term "epoxide" means a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

As used herein, the expression, "liquid-phase" refers to a continuous intermediate phase between gas phase and a solid phase that may optionally comprise a minor amount of gas and/or solid discrete phase(s). The liquid phase may comprise one or more immiscible liquid phases and may contain one or more dissolved solids, such as one or more acids, bases, or salts.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases, two or more liquid discrete phases, and/or two or more solid discrete phases.

As used herein, the expression "liquid-vapor contacting device" refers to devices that serve to provide the contacting and development of at least one interfacial surface between liquid and vapor in the device. When the liquid-vapor contacting device is intended for distilling and/or fractionating the components of a feedstream, the liquid-vapor contacting device (41) preferably has a bottom end generally indicated by numeral (42) and a top end, generally indicated by numeral (43) suitable for applying a gradually decreasing temperature gradient from the bottom end to the top end to substances within the column. Examples of liquid-vapor contacting devices include plate column, packed column, wetted-wall (falling film) column, spray chamber, heat exchanger or any combination thereof. Examples of devices comprising plate columns and packed columns include distillation columns, fractionation columns, and stripping columns.

As used herein, the expression "liquid distributor" means a device that spreads the liquid uniformly across the top of the packing in a packed bed column. Uniform distribution of liquid at the top of the packed bed is important for efficient column operation.

As used herein, the term "cooling device" means a system for removing heat from a process fluid via a secondary fluid physically separated from the process fluid, such as a condenser. The process fluid and the secondary fluid may each be a vapor, a liquid, or a combination of liquid and vapor. Cooling may be a unit operation external to a distillation column or it may be a unit operation internal to a distillation column. The physical separation may be in the form of tubes and the condensation may be carried out on the inside or outside of the tubes. Cooling preferably comprises nonadiabatic cooling and the cooling device is therefore preferably a nonadiabatic cooling device.

Mixture Processed in Step (a)

The mixture processed in step (a) may be obtained directly or indirectly from any hydrochlorination process well-known in the art. For example, German Patent No. 197308 teaches a process for preparing a chlorohydrin by the catalytic hydrochlorination of glycerin by means of anhydrous hydrogen chloride. WO 2005/021476 discloses a continuous process for preparing the dichloropropanols by hydrochlorination of glycerin and/or monochloropropanediols with gaseous hydrogen chloride with catalysis of a carboxylic acid. WO 2006/020234 A1 describes a process for conversion of a glycerol or an ester or a mixture thereof to a chlorohydrin, comprising the step of contacting a MAHC, an ester of a MAHC, or a mixture thereof with a source of a superatmospheric partial pressure of hydrogen chloride to produce a chlorohydrin, an ester of a chlorohydrin, or a mixture thereof in the presence of an organic acid catalyst without substantially removing water. The above references are hereby incorporated herein by reference with respect to the above-described disclosures.

In an exemplifying hydrochlorination process, MAHC and a hydrochlorination catalyst are charged to the hydrochlorination reactor. Then a chlorinating agent such as hydrogen chloride is added to the reactor. The reactor pressure is adjusted to the desired pressure and the reactor contents are heated to the desired temperature for the desired length of time. After completion of the hydrochlorination reaction or while carrying out the hydrochlorination reaction, the reactor contents as a reaction effluent stream is discharged from the reactor and fed directly, or indirectly via another reactor or other intervening step, to a separation system comprising a DCH recovery system according to the present invention and optionally including other separation systems or equipment, such as a flash vessel and/or reboiler.

The hydrochlorination reaction above may be carried out in one or more hydrochlorination reactor vessels such as a single or multiple continuous stirred tank reactors (referred to hereafter by the abbreviation "CSTR"), single or multiple tubular reactor(s), plug flow reactors (referred to hereafter by the abbreviation "PFR"), or combinations thereof. The hydrochlorination reactor can be, for example, one reactor or multiple reactors connected with each other in series or in parallel including, for example, one or more CSTRs, one or more tubular reactors, one or more PFRs, one or more bubble column reactors, and combinations thereof.

In a preferred embodiment, part or all of the hydrochlorination effluent stream is a feed stream from a PFR. A PFR is a type of reactor that has a high length/diameter (L/D) ratio and has a composition profile along the length of the reactor. The concentration of the reactants being fed into the PFR decreases from inlet to the outlet along the flow path of the PFR and the concentration of the products or the intermediate products increases from inlet to the outlet along the flow path of the PFR. In the case of hydrochlorination of glycerol, the concentration of HCl and glycerol decreases from inlet of the PFR to outlet of the PFR while the total concentration of chlorohydrins increases from inlet of the PFR to the outlet of the PFR.

The equipment useful for conducting the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals such as tantalum, suitable metallic alloys (particularly nickel-molybdenum alloys such as Hastalloy C®), or glass-lined equipment, for example.

In addition to DCH(s), one or more of the unreacted MAHC(s) and/or chlorination agent(s), reaction intermediates such as MCH(s), MCH ester(s), and/or DCH ester(s), catalyst(s), ester(s) of catalyst(s), water, and/or heavy byproduct(s) may be present in mixture (a). A recycle process is preferred in which one or more of the unreacted MAHC(s), ester(s) of MAHC(s) and/or chlorination agent(s), reaction intermediates such as MCH(s), MCH ester(s), DCH ester(s), and other substances such as catalyst(s) and ester(s) of catalyst(s), are preferably recycled to a prior step in the process, such as to at least one hydrochlorination reactor for further hydrochlorination. In particular, a liquid higher boiling fraction comprising a residue of the distilling or fractionating step containing one or more of MAHC(s), MCH(s), catalyst(s), and/or ester(s) of one or more MAHC(s), MCH(s), DCH(s) and/or catalyst(s), and preferably a combination of two or more thereof, is recycled to the hydrochlorination step, such as by recycling the higher boiling fraction to one or more reactor(s). Such recycle process(es) is preferably continuous. In this manner, raw material efficiencies are maximized and/or catalysts are reused.

When catalysts are reused in such a process scheme, it may be desirable to employ the catalysts in a higher concentration than they are employed in a single-pass process. This may result in faster reactions, or smaller process equipment, which results in lower capital costs for the equipment employed.

In a continuous recycle process, undesirable impurities and/or reaction byproducts may build up in the process. Thus, it is desirable to provide a means for removing such impurities from the process, such as via one or more purge outlets, for example, or by a separation step. Furthermore, a purged stream may be further treated to recover a useful portion of the purged stream.

The chlorinating agent that may optionally be present in the mixture treated according to the present invention is preferably hydrogen chloride or hydrogen chloride source, and may be a gas, a liquid or in a solution, or a mixture thereof. The hydrogen chloride is preferably introduced in the gaseous state and, when the hydrochlorination reaction mixture is in the liquid phase, at least some of the hydrogen chloride gas is preferably dissolved in the liquid reaction mixture. The hydrogen chloride may, however, be diluted in a solvent, such as an alcohol (for example methanol), or in a carrier gas such as nitrogen, if desired.

It is preferred that the hydrochlorination step of the present invention be carried out under superatmospheric pressure conditions. "Superatmospheric pressure" herein means that the hydrogen chloride (HCl) partial pressure is above atmospheric pressure, i.e. 15 psia (103 kPa) or greater. Generally, the hydrogen chloride partial pressure employed in the hydrochlorination process is at least about 15 psia (103 kPa) or greater. Preferably, the hydrogen chloride partial pressure employed in the hydrochlorination process is not less than about 25 psia (172 kPa), more preferably not less than about 35 psia (241 kPa), and most preferably not less than about 55 psia (379 kPa); and preferably not greater than about 1000 psia (6.9 MPa), more preferably not greater than about 600 psia (4.1 MPa), and most preferably not greater than about 150 psia (1.0 MPa).

It is also preferred to conduct the hydrochlorination step at a temperature sufficient for hydrochlorination that is also below the boiling point of the chlorohydrin(s) in the reaction mixture having the lowest boiling point for a given pressure condition during the hydrochlorination step in order to keep the chlorohydrin(s) produced and converted during hydrochlorination in the liquid phase of the reaction mixture for recovery in steps (b) and (c). The upper limit of this preferred temperature range may be adjusted by adjusting the pressure condition. A higher pressure during hydrochlorination may be selected to increase the boiling point temperature of the chlorohydrin(s) in the reaction mixture, so that the preferred temperature range for keeping DCH(s) in the liquid phase may be increased by increasing the pressure condition.

Preferably, less than 50, more preferably less than 10, even more preferably less than 5, and yet more preferably less than 1, percent of the DCH present in the hydrochlorination effluent is removed from the hydrochlorination effluent prior to step (b).

The hydrochlorination effluent comprises one or more DCHs, one or more compounds comprising ester(s) of DCH(s), MCH(s) and/or ester(s) thereof, and MAHC(s) and/or ester(s) thereof, and optionally one or more substances comprising water, chlorination agent(s), catalyst(s) and/or ester(s) of catalyst(s). Additional optional components may also be present in the effluent depending on the starting materials, reaction conditions, and any process steps intervening between the hydrochlorination reaction and recovery of DCH according to the present invention. The hydrochlorination effluent is preferably in the liquid phase as the hydrochlorination effluent is withdrawn from the hydrochlorination step and/or reactor and the mixture provided in step (a) comprises at least part of the liquid-phase effluent of the hydrochlorination step.

In a preferred embodiment, at least one MAHC and/or ester thereof is present in the mixture provided in step (a). When MAHC(s) and/or ester(s) thereof is/are present in the mixture provided in step (a), the same MAHC(s) and/or ester(s) thereof may also be present in the high-boiling fraction of step (b).

MAHCs found in the effluent treated according the present invention may include for example 1,2-ethanediol; 1,2-propanediol; 1,3-propanediol; 3-chloro-1,2-propanediol; 2-chloro-1,3-propanediol; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the MAHCs in the effluents treated according to the present invention include for example 1,2-ethanediol; 1,2-propanediol; 1,3-propanediol; and 1,2,3-propanetriol; with 1,2,3-propanetriol being most preferred.

Examples of esters of MAHCs found in the effluents treated according to the present invention include for example ethylene glycol monoacetate, propanediol monoacetates, glycerin monoacetates, glycerin monostearates, glycerin diacetates, and mixtures thereof. In one embodiment, such esters can be made from mixtures of MAHC with exhaustively esterified MAHC, for example mixtures of glycerol triacetate and glycerol.

In the same or another preferred embodiment, at least one MCH and/or ester thereof is present in the mixture provided in step (a). When MCH(s) and/or ester(s) thereof is/are present in the mixture provided in step (a), the same MCH(s) and/or ester(s) thereof may also be present in the high-boiling fraction of step (b).

The MCHs generally correspond to the hydrochlorinated MAHCs in which one of a pair of hydroxyl groups covalently bonded to two separate vicinal carbon atoms is replaced by a covalently bonded chlorine atom. The ester(s) of MCH may be the result of hydrochlorination of MAHC ester(s) or reaction with an acid catalyst, for example.

The DCHs generally correspond to the hydrochlorinated MAHCs in which two hydroxyl groups covalently bonded to two separate carbon atoms, at least one of which is vicinal to a third carbon atom having a hydroxyl group, are each replaced by a covalently bonded chlorine atom. The ester(s) of DCH(s) may be the result of hydrochlorination of MAHC ester(s), MCH ester(s) or reaction(s) with acid catalyst(s), for example.

In an embodiment of the present invention where MAHC(s) is/are the starting material fed to the process, as opposed to ester(s) of MAHC(s) or a mixture of MAHC(s) and ester(s) thereof as a starting material, it is generally preferred that the formation of chlorohydrin be promoted by the presence of one or more catalyst(s) and/or ester(s) thereof. Catalyst(s) and/or ester(s) thereof may also be present where ester(s) of MAHC(s), or a mixture of MAHC(s) and ester(s) thereof, is a starting material to further accelerate the hydrochlorination reaction.

Carboxylic acids, RCOOH, catalyze the hydrochlorination of MAHCs to chlorohydrins. The specific carboxylic acid catalyst chosen may be based upon a number of factors including for example, its efficacy as a catalyst, its cost, its stability to reaction conditions, and its physical properties. The particular process, and process scheme in which the catalyst is to be employed may also be a factor in selecting the particular catalyst. The "R" groups of the carboxylic acid may be independently chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

The carboxylic acids useful as hydrochlorination catalysts may be monobasic such as acetic acid, formic acid, propionic acid, butyric acid, isobutyric acid, hexanoic acid, 4-methylvaleric acid, heptanoic acid, oleic acid, or stearic acid; or polybasic such as succinic acid, adipic acid, or terephthalic acid. Examples of aralkyl carboxylic acids include phenylacetic acid and 4-aminophenylacetic acid. Examples of substituted carboxylic acids include 4-aminobutyric acid, 4-dimethylaminobutyric acid, 6-aminocaproic acid, 6-hydroxyhexanoic acid, 6-chlorohexanoic acid, 6-aminohexanoic acid, 4-aminophenylacetic acid, 4-hydroxyphenylacetic acid, lactic acid, glycolic acid, 4-dimethylaminobutyric acid, and 4-trimethylammoniumbutyric acid. Additionally, materials that can be converted into carboxylic acids under reaction conditions, including for example carboxylic acid halides, such as acetyl chloride, 6-chlorohexanoyl chloride, 6-hydroxyhexanoyl chloride, 6-hydroxyhexanoic acid, and 4-trimethylammonium butyric acid chloride; carboxylic acid anhydrides such as acetic anhydride and maleic anhydride; carboxylic acid esters such as methyl acetate, methyl propionate, methyl pivalate, methyl butyrate, ethylene glycol monoacetate, ethylene glycol diacetate, propanediol monoacetates, propanediol diacetates, glycerin monoacetates, glycerin diacetates, glycerin triacetate, and glycerin esters of a carboxylic acid (including glycerin mono-, di-, and tri-esters); MAHC acetates such as glycerol 1,2-diacetate; carboxylic acid amides such as ε-caprolactam and γ-butyrolactam; and carboxylic acid lactones such as γ-butyrolactone, δ-valerolactone and ε-caprolactone may also be employed in the present invention Zinc acetate is an example of a metal organic compound. Mixtures of the foregoing catalysts and catalyst precursors may also be used.

When a catalyst is used in the superatmospheric pressure process, the catalyst may be for example a carboxylic acid; an anhydride; an acid chloride; an ester; a lactone; a lactam; an amide; a metal organic compound such as sodium acetate; or a combination thereof. Any compound that is convertible to a carboxylic acid or a functionalized carboxylic acid under hydrochlorination reaction conditions may also be used. A preferred carboxylic acid for the superatmospheric pressure process is an acid with a functional group consisting of a halogen, an amine, an alcohol, an alkylated amine, a sulfhydryl, an aryl group or an alkyl group, or combinations thereof, wherein this moiety does not sterically hinder the carboxylic acid group.

Certain catalysts may also be advantageously employed at superatmospheric, atmospheric or sub-atmospheric pressure, and particularly in circumstances where water is continuously or periodically removed from the reaction mixture to drive conversion to desirably higher levels as may be the case when recovering DCH(s) according to the claimed invention.

For example, the hydrochlorination of MAHC(s) reaction can be practiced by introducing hydrogen chloride gas into contact with a mixture of MAHC(s) and catalyst(s), such as by sparging the hydrogen chloride gas through a liquid-phase reaction mixture. In such a process, the use of less volatile catalysts, such as 6-hydroxyhexanoic acid, 4-aminobutyric acid; dimethyl 4-aminobutyric acid; 6-chlorohexanoic acid; caprolactone; carboxylic acid amides such as ε-caprolactam and γ-butyrolactam; carboxylic acid lactones such as γ-butyrolactone, δ-valerolactone and ε-caprolactone; caprolactam; 4-hydroxyphenyl acetic acid; 6-amino-caproic acid; 4-aminophenylacetic acid; lactic acid; glycolic acid; 4-dimethylamino-butyric acid; 4-trimethylammoniumbutyric acid; and combination thereof; and the like may be preferred. It is most desirable to employ a catalyst, under these atmospheric or subatmospheric conditions, that is less volatile than the DCH(s) produced and recovered.

Preferred catalysts used in the present invention include carboxylic acids, esters of carboxylic acids, and combinations thereof, particularly esters and acids having a boiling point higher than that of the desired highest boiling DCH that is formed in the reaction mixture (i.e., the catalyst(s) is/are preferably less volatile than the DCH(s) in the mixture), so that the DCH(s) can be removed without removing the catalyst. Catalysts which meet this definition and are useful in the present invention include for example, polyacrylic acid, glycerin esters of carboxylic acids (including glycerin mono-, di-, and tri-esters), polyethylene grafted with acrylic acid, divinylbenzene/methacrylic acid copolymer, 6-chlorohexanoic acid, 4-chlorobutanoic acid, caprolactone, heptanoic acid, 4-hydroxyphenylacetic acid, 4-aminophenylacetic acid, 6-hydroxyhexanoic acid, 4-aminobutyric acid, 4-dimethylaminobutyric acid, 4-trimethyl-ammoniumbutyric acid chloride, stearic acid, 5-chlorovaleric acid, 6-hydroxyhexanoic acid, 4-aminophenylacetic acid, and mixtures thereof. Carboxylic acids that are sterically unencumbered around the carboxylic acid group are generally preferred.

Furthermore, the catalyst(s) is/are preferably miscible with the MAHC(s) employed. For this reason, the catalyst(s) may contain polar heteroatom substituents such as hydroxyl, amino or substituted amino, or halide groups, which render the catalyst miscible with the MAHC(s) in the reaction mixture, such as glycerol.

One embodiment of the catalyst(s) that may be present is generally represented by Formula (a) shown below wherein the functional group "R'" includes a functional group comprising an amine, an alcohol, a halogen, a sulfhydryl, an ether; or an alkyl, an aryl or alkaryl group of from 1 to about 20 carbon atoms containing said functional group; or a combination thereof; and wherein the functional group "R" may include a hydrogen, an alkali, an alkali earth or a transition metal or a hydrocarbon functional group.

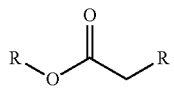

Formula (a)

Where the catalyst is recycled and used repeatedly, such recycled catalysts may be present in an amount from about 0.1 mole %, preferably from about 1 mole %, more preferably from about 5 mole %, up to about 99.9 mole %, preferably up to 70 mol %, and more preferably up to 50 mole %, based on the amount in moles of MAHC present. Higher catalysts concentrations may be desirably employed to reduce the reaction time and minimize the size of process equipment.

In a preferred embodiment, the mixture distilled or fractionated in step (a) comprises water, such as the water produced as a co-product of the hydrochlorination reaction, water present in the starting materials for the hydrochlorination reaction, and/or water introduced as the stripping agent. The mixture may contain at least 1 weight-percent, or at least 5 weight-percent water, but less than the weight-percent of water at the azeotropic composition of the dichlorohydrin-water mixture or the dichlorohydrin-water-hydrogen chloride mixture at the distillation pressure, preferably up to 50 weight-percent, more preferably up to 20 weight-percent, and most preferably up to 10 weight-percent water.

The mixture distilled or fractionated in step (a) may be a liquid phase or a combination of liquid-phase and vapor phase. In one embodiment, the mixture distilled or fractionated in step (a) is provided to step (a) by separating a hydrochlorination reaction effluent stream into a vapor-phase effluent stream and a liquid-phase effluent stream prior to step (a) and introducing the liquid-phase effluent stream, or both the vapor-phase effluent stream and the liquid-phase effluent stream, separately or combined, into step (a). The separation of the reaction effluent stream in step (a) of the process may be carried out in, for example, in a separation system comprising a liquid-vapor contacting device and, optionally, with a flash vessel separate from or integral with the liquid-vapor contacting device.

Recovery of DCH from the Mixture
Distilling/Fractionating Step(A)

Recovering DCH(s) from the mixture comprises distilling or fractionating the mixture under reflux conditions to separate from the mixture a first vapor phase effluent stream comprising one or more of the above-identified DCH(s) and water having a first temperature equal to or greater than the boiling point of the DCH(s) and water present in the mixture at the pressure of the first vapor phase effluent. The DCH(s) preferably comprise(s) 1,3-dichloro-2-propanol and/or 2,3-dichloro-1-propanol).

The first vapor phase effluent stream may contain one or more of the above-identified MCH(s), such as 2-chloro-1,3-propanediol and/or 3-chloro-1,2-propanediol, and ester(s) thereof; one or more of the above-identified MHAC(s); and/or one or more of the above-identified substances comprising chlorinating agent(s), catalyst(s), and/or ester(s) of catalyst(s). Distilling or fractionating step (a) enriches the concentration of DCH(s) in the first vapor phase effluent stream relative to the mixture fed to the distilling or fractionating step.

Distillation or fractionation step (a) is preferably carried out at a temperature measured in the distillation bottoms of at least 25° C., more preferably at least 50° C., yet more preferably at least 80° C., even more preferably at least 100° C., and yet even more preferably at least 110° C., up to 160° C., preferably up to 150° C., even more preferably up to 140° C., yet even more preferably up to 130° C., and most preferably up to 120° C. The lower temperatures help minimize the rate of formation of the higher molecular weight compounds, called heavies, in the process and conversely, the higher temperatures increase the rate of formation of the heavies. The lower bottom temperature also reduces the risk of a runaway reaction in the case of a process upset such as loss of vacuum or loss of power to the plant.

One method of achieving low temperature in the bottom of the column is operating the column under a vacuum condition such that the pressure in the top of the column is maintained at less than 100 kPa, preferably less than 50 kPa, more preferably less than 10 kPa, and most preferably less than 5 kPa and greater than 0.1 kPa, preferably greater than 0.5 kPa and most preferably greater than 1 kPa. Lower pressure in the column helps achieve lower temperature in the bottom of the column, but this must be balanced with increased column size as well as increased operating cost required at lower pressures. Increased column size results in increased capital cost of the column and the column internals.

To one embodiment of the process of the present invention step (a) is carried out at a pressure in the range from 0.1 kPa to 100 kPa; preferably, in the range from 1 kPa to 20 kPa; and about preferably in the range from 1 kPa to 10 kPa.

The preferred reduced pressure condition may be generated by applying vacuum directly or indirectly to the mixture undergoing distillation or fractionation in step (a) to produce the first vapor-phase effluent stream. The vacuum is preferably applied to the third vapor-phase effluent stream downstream from the second cooling step (e). The vacuum is preferably applied using any appropriate means for generating vacuum, such as a vacuum pump or a steam ejector.

The percent DCH(s) recovered from the mixture fed into step (a) generally depends on the combination of temperature and pressure conditions selected. To obtain a given DCH recovery in step (a), a reduction in temperature generally requires a reduction in operating pressure and, conversely, an increase in operating pressure generally requires an increase in operating temperature to obtain a given percent DCH recovery rate. The specific temperature and pressure conditions selected will depend on the extent to which realization of the respective benefits relating to low temperature and higher pressure operation is desired.

Step (a) is preferably carried out under conditions such that the amount of heavy byproducts in the high boiling fraction of step (a) does not exceed 120 percent, more preferably does not exceed 110 percent, even more preferably does not exceed 105 percent, and most preferably does not exceed 102 percent of the amount of heavy byproducts in the mixture fed into step (a). Minimizing the heavy and undesired byproducts formation in the process allows reducing the process purge required to prevent buildup of heavy byproducts in the process when operating the process as a continuous recycle process. The purge stream may contain usable components in the process such as dichlorohydrins, monochlorohydrins, MAHCs, catalyst, and/or their esters. Therefore, minimizing the purge results in increased yield of dichlorohydrins.

When the chlorinating agent is hydrogen chloride, for example, most of the hydrogen chloride is removed from the mixture during step (a), because it is lighter (i.e., has a lower boiling point or has a higher vapor pressure) than water, chlorohydrin(s), heavies, etc., of the feed stream fed to step (1).

The feed stream provided in step (a) may be passed through a pressure letdown step prior to distilling and/or fractionating the mixture, such as via an intervening flash vessel, to reduce the pressure of the stream and flashing tendency during distillation and/or fractionation. The flash vessel may act also as a surge or a buffer vessel to reduce impact of flow fluctuations or surges upstream from the distillation and/or fractionation step, and help regulate the flow of the mixture into the distillation and/or fractionation step at a relatively constant rate.

The distillation or fractionation step (a) is preferably carried out in at least one liquid-vapor contacting device, such as at least one distillation or fractionation column (preferably one fractional distillation column and/or a packed column), preferably having a source of heat at the bottom end of the liquid-vapor contacting device and a means for applying a vacuum to the top end of the liquid-vapor contacting device. Examples of distillation columns suitable for use as the liquid-vapor contacting device include plate or tray columns, bubble cap columns and packed columns. The liquid-vapor contacting device is operated under reflux conditions.

In one embodiment, additional MAHC(s) and/or ester(s) thereof may be introduced into step (a) for reactive distillation/fractionation. The additional MAHC(s) and/or ester(s) thereof may react with the chlorination agent to produce additional MCH(s) and/or ester(s) thereof. Additional MAHC(s) may also react with ester(s) of DCH(s) and MCH(s) to convert them to non-ester(s) to facilitate recovery of DCH(s). The additional MAHC(s) and/or ester(s) thereof is/are preferably introduced as a liquid phase into a reflux to provide additional liquid phase for reflux.

The mixture fed into step (a) is distilled or fractionated in step (a) to separate a first vapor-phase effluent comprising at least DCH(s) and water from the liquid-phase mixture of step (a). The first vapor-phase effluent of step (a), which may also contain other low-boiling or azeotropic components of the mixture fed into step (a), such as the chlorinating agent, is condensed to form a first condensed liquid-phase effluent stream comprising at least DCH(s) according to step (b). The first condensed liquid-phase effluent stream is separated into a first fraction and a second fraction. The first fraction of the first condensed liquid-phase effluent stream is recycled to the distilling or fractionating step (a) according to step (d). Recycling the first fraction of step (c) according to step (d) provides liquid for reflux during distillation or fractionation according to step (a).

Partially Condensing the First Vapor-Phase Effluent

The DCH-rich first vapor phase effluent produced via distilling or fractionating the above-described mixture under reflux conditions according to step (a) is cooled nonadiabatically to a second temperature lower than the first temperature of step (a) to condense a fraction of the first vapor phase effluent stream of step (a) to produce a first condensed liquid-phase effluent stream and a second vapor phase effluent stream having the second temperature.

The second temperature of step (b) is below the dew point of the first vapor-phase effluent stream at the operating pressure of step (b) and preferably greater, more preferably at least 1 degree Celsius greater, than the dew point of water at the operating pressure of step (b). The second temperature is preferably at least 5° C., more preferably at least 10° C., and most preferably at least 20° C., and up to 60° C., more preferably up to 50° C., and even more preferably up to 40° C., below the first temperature of step (a).

In one embodiment, step (b) is conducted using a first nonadiabatic cooling device, such as an evaporative condenser or a water-cooled condenser, using water from a cooling pond and/or a fluid cooling medium, such as water, used upstream as the fluid cooling medium in the second cooling step (e). It is advantageous to select the second temperature such that the nonadiabatic cooling can be provided by water from a cooling pond or cooling tower instead of using chilled water. This saves energy that is otherwise required in refrigeration when using chilled water and accomplishes the cooling with minimum energy use.

The first vapor-phase effluent stream comprises organic compounds and water and optionally the chlorinating agent.

The first condensed liquid-phase effluent stream contains more than 50 weight-percent, preferably more than 60 weight-percent, more preferably more than 70 weight-percent, even more preferably more than 80 weight percent, yet even more preferably more than 90 weight-percent, most preferably more than 95 weight-percent and yet even more preferably more than 99 weight-percent, DCH(s). The high purity DCH(s), such as 99 weight-percent DCH(s), that can be obtained allows using such DCH(s) without requiring any further purification in a process where high purity DCH(s) is preferred or required. The high purity DCH can be advantageously used directly (i.e., preferably without any intervening purifying unit operations, more preferably without any intervening unit operations) in epoxidation of Bisphenol to produce liquid epoxy resin.

In step (d), the first fraction of the first condensed liquid-phase effluent stream produced in step (b) is recycled to step (a) as reflux for step (a). The ratio of mass flow rate of the first fraction of the first condensed liquid-phase effluent stream recycled to step (a) as reflux for step (a) relative to mass flow rate of the total first condensed liquid-phase effluent stream condensed during step (b) is preferably at least 0.1:1 and up to 0.8:1, preferably up to 0.5:1, more preferably up to 0.4:1, and even more preferably up to 0.3:1. In one embodiment, the ratio is for the range of from 0.1:1 to 0.4:1. This ratio determines the reflux ratio for the column.

When using packed columns and low reflux ratios which results in low reflux rates, it is desirable to employ liquid distributors that are suitable for low liquid loading. Liquid loading is defined as liquid mass flow rate per unit cross sectional area of the distillation or fractionation column DCHs have much lower heat of vaporization compared with water. Therefore if aqueous-rich liquid is used for reflux in the distillation column instead of the DCH-rich organic liquid, then the reflux ratio would be even smaller which would result in even smaller liquid flow rates from the liquid distributor requiring special liquid distributors that are suitable for such low liquid loading. Therefore, using DCH rich liquid for reflux according to the present invention provides greater choice in the design and selection of the appropriate liquid distributor. This greater choice is especially advantageous in a corrosive process such as this process.

The first condensed liquid-phase effluent stream is preferably accumulated prior to recycling it into step (a) to facilitate good control/optimization of the reflux flow rate over time and thereby reduce fluctuations in step (a) operating conditions and/or first vapor phase effluent output. The accumulation is preferably conducted by means of a reservoir between step (b) and step (c) as further described below with reference to the illustrative drawings.

Partially Condensing the Second Vapor-Phase Effluent Stream

The second vapor phase effluent stream of step (b) is cooled, preferably non-adiabatically, to a third temperature lower than the second temperature of the second vapor phase effluent stream to condense at least a fraction of the second vapor phase effluent stream of step (b) to produce a second condensed liquid-phase effluent stream and a third vapor phase effluent stream having the third temperature, In the process for recovering DCH(s) according to the present invention, the third temperature of cooling step (e) is preferably below, more preferably at least 1 degree Celsius below, and even more preferably at least 5 degrees Celsius below, the dew point of water at the operating pressure of cooling step (e). The third temperature is preferably at least 10° C., more preferably at least 20° C., and even more preferably at least 30° C. below the second temperature of cooling step (b). The third temperature is preferably selected such that at least 80 mass percent, more preferably at least 90 mass percent, even more preferably at least 95 mass percent and most preferably at least 99 mass percent of the second vapor phase effluent stream is condensed to achieve the highest total recovery of DCH(s).

In one embodiment, step (e) is conducted using a cooling device, such as the cooling device described above as suitable for use in step (b). The fluid cooling medium may be water from a cooling pond if it is available at a low enough temperature and/or a refrigerated fluid cooling medium such as chilled water or chilled glycol, or the refrigerant itself. In a preferred embodiment, chilled water or chilled glycol or such low temperature coolants are used to obtain a high recovery of DCHs.

The volumetric ratio of the first condensed liquid-phase produced in step (b) to the second condensed liquid-phase produced in step (e) is preferably at least 1:1, more preferably at least 3:1, even more preferably at least 5:1, up to 100:1, more preferably up to 50:1, and even more preferably up to 40:1.

In one embodiment, the ratio of the mass flow rate at which the first vapor-phase effluent stream is condensed in step (b) to the mass flow rate at which the second vapor-phase effluent stream is condensed in step (e) is in the range from 1:1 to 100:1; preferably in the ranges from 1:1 to 10:1; and where preferably in the range from 1:1 to 2:1.

Processing the Condensed Liquid-Phase Effluent Streams Downstream

The second fraction of the first condensed liquid phase effluent stream produced during step (b) and separated in step (c) may be subjected to further processing steps. Depending on the further processing steps, the second fraction may be used to supply DCH(s) for chemical conversion of DCH(s) into other compounds without further processing. The liquid phase may be used in processes for conversion of DCH(s) into other industrially useful chemical products.

The second fraction separated in step (c) may, for example, be subjected to epoxidation to form epichlorohydrin without additional purification of the dichlorohydrin(s). The epoxidation may be carried out by contacting one or more effluent streams comprising DCH(s) with a base, such as alkali metal hydroxide (e.g., sodium hydroxide) or alkaline earth metal hydroxide (e.g., calcium hydroxide or calcium carbonate) to form epichlorohydrin(s) and alkali metal chloride salt(s) or alkaline earth metal chloride salt(s), respectively.

In one embodiment, the second condensed liquid-phase effluent stream comprises an aqueous phase and an organic phase. Phase separation in the liquid generating an aqueous rich and an organic rich phases depends on the concentration of HCl in the liquid, the temperature and the overall composition of the liquid. Phase separation is most prone to occur when HCl concentration in the liquid is lower. In the case of phase separation, the organic phase and the aqueous phase of the second condensed liquid-phase effluent stream are preferably separated from each other, so that the flow and composition of the two phases to the downstream process can be controlled at relatively constant values for better control in the downstream process or they may be used separately downstream. In particular, the separated aqueous phase may be used in the epoxidation step to recover and convert DCH(s) remaining in the separated aqueous phase as well as to provide additional water for maintaining concentration of salts below saturation condition in the epoxidation step.

The separated organic phase obtained from the second condensed liquid-phase effluent stream may be used in a downstream epoxidation process to supply additional recovered DCH(s) independent from, or preferably combined with, the use of the second fraction of the first condensed liquid-phase effluent stream in a downstream epoxidation process. In one embodiment, the organic phase obtained from the second condensed liquid-phase effluent stream is combined, or admixed, with the second fraction of the first condensed liquid-phase effluent stream and the combined effluent streams are subjected to epoxidation as described above.

Separation of the aqueous phase and the organic phase may be carried out using a liquid-liquid separation device such as those conventional in the art. An example of a liquid-liquid separation device is a decanter.

Variations and Advantages

The Above Process Steps May Be Carried Out Independently Or Simultaneously with one another. In a preferred embodiment, one or more of the above process steps is carried out simultaneously with one another.

One or more of the above process steps may be carried out continuously or discontinuously. One or more of the above process steps are preferably carried out continuously (i.e., without interruption). Preferably, all the above process steps are carried out continuously. The process may be carried out for a predetermined period of time, for example for a time period of about one hour or more.

The process according to the present invention may recover at least 80 percent, more preferably at least 90 percent, even more preferably at least 95 percent, yet more preferably at least 99 percent, and yet even more preferably at least 99.9 percent of the DCH(s) produced during hydrochlorination.

These high recovery rates are obtained at a greater efficiency than that obtained using state of the art methods. The process is more energy efficient because first condenser can use cooling water and only the second condenser may require chilled water or chilled glycol or such other appropriate coolant. Therefore, it is preferred to maximize the condensation in the first of the two partial condensers.

Using DCH-rich liquid for reflux instead of water-rich liquid makes the liquid distributor design and selection easier as the reflux flow rate is not too small A very small reflux flow rate requires specially designed liquid distributors in the distillation column which can be very expensive in a highly corrosive process such as this as it requires highly specialized materials of construction. Using DCH-rich liquid for reflux to increase the reflux mass flowrate is achieved without requiring more energy for distillation of DCH(s).

Apparatus

The above process may be conducted using an apparatus according to the present invention. The apparatus is now described in more detail in reference to FIG. 1.

FIG. 1 is a schematic diagram showing the main features of an illustrative apparatus that may be used and their respective feed streams. The apparatus of FIG. 1 for producing DCH, generally indicated by numeral (10), comprises a reactor system generally indicated by numeral (30) comprising one or more reactors (31) connected in series or in parallel. The reactors may be selected from various known reactors, such as CSTRs, tubular reactors, and PFRs, and combinations thereof. When multiple reactors are present, the reactors may be connected to each other in series or parallel. The reactor system (30) is connected directly or indirectly to a first feed stream (32) comprising MAHC(s) and a second feed stream (33) comprising chlorinating agent.

The reactor system (30) is connected directly or indirectly to a separation system generally indicated by numeral (40) for conducting at least part of a liquid-phase reactor effluent feed stream (34) from the reactor system (30) to the separation system (40).

The separation system (40) comprises at least one liquid-vapor contacting device (41) for distillation and/or fractionation of the reactor effluent feed stream (34) and optionally one or more flash vessels (not shown).

The liquid-vapor contacting device (41) preferably has a bottom end generally indicated by numeral (42) and a top end generally indicated by numeral (43) for applying a gradually decreasing temperature gradient from the bottom end (42) to the top end (43) to substances within the liquid-vapor contacting device. The at least one liquid-vapor contacting device (41) of the at least one separation system (40) is preferably a distillation or fractionation column, such as a packed distillation column and/or a distillation column adapted for carrying out fractional distillation under reflux conditions having a reflux zone for carrying out reflux.

The separation system (40) has a vapor phase effluent outlet for removal of vapor phase from the separation system (40), which is preferably located proximal to the top end (43) of the at least one liquid-vapor contacting device (41), and a liquid phase effluent outlet for removal of liquid phase from the separation system (40), which is preferably located proximal to the bottom end (42) of the at least one liquid-vapor contacting device (41).

The separation system (40) may comprise one or more flash vessels (not shown). The reactor system (30) is preferably connected to the at least one liquid-vapor contacting device (41) of the at least one separation device (40) via the at least one flash vessel, whereby the reactor effluent feed stream (34) is separated into a vapor phase and a liquid phase in the flash vessel by reducing the pressure on the liquid phase. The separated liquid phase and vapor phase may be introduced into the at least one liquid-vapor contacting device (41) of the separation system (40) for distillation or fractionation.

The separation system (40) also preferably comprises a reboiler (not shown) connected to the bottom end (42) of the at least one liquid-vapor contacting device (41) of the separation system (40) for heating the liquid phase in the bottom end (42) of the at least one liquid-vapor contacting device (41) of the separation system (40).

The at least one liquid-vapor contacting device (41) of the separation system (40) is optionally connected directly or indirectly to at least one source of stripping agent for introducing one or more stripping agents into the bottom end (42) of the at least one liquid-vapor contacting device (41) of the separation system (40).

The separation system (40) is preferably connected to the reactor system (30) for conducting a distillation residue recycle stream (44, 45) comprising a distillation residue stream (44) from the separation system (40) to the reactor system (30). The recycle feed stream (44 45) preferably has a distillation residue recycle purge (46) for removal of heavy byproducts from the distillation residue recycle feed stream (44, 45).

The top end (43) of the liquid-vapor contacting device (41) is connected to a first condensation system generally indicated by numeral (50) comprising a first cooling device (51) for conducting a vapor phase effluent stream (47) from the separation system (40) to the first condensation system (51).

The first condensation system (50) comprises a first cooling device (51) and, optionally, a first reservoir (52) connected to the first cooling device (51) for accumulation of condensate from the first cooling device (51).

The first cooling device (51) is a cooling device suitable for cooling the vapor phase effluent stream (47) from a first temperature at or above the dew point of the first vapor-phase effluent stream (47) to a second temperature below the dew point of the first vapor-phase effluent stream (47) and above the dew point of water at the operating pressure of the cooling device (51). The first cooling device (51) is preferably a nonadiabatic cooling device.

The cooling device (51) is preferably one or more condensers. The condensers preferably comprise one or more coolant passages made of heat-conductive material, for conducting a fluid, such as an aqueous liquid, having a temperature at or below the above-mentioned second temperature. The optional first reservoir (52) is preferably adapted to receive condensate from one or more condensers of cooling device (51).

The first condensation system (50) is connected to the separation system (40) for recycling a fraction of condensed liquid-phase effluent stream (53) from the first condensation system (50) to the separation system (40) via a condensed liquid-phase recycle stream (54, 55). The condensed liquid-phase recycle stream (54, 55) is preferably conducted to at least one liquid-vapor contacting device for distillation and/or fractionation. In particular, the condensed liquid-phase recycle stream (54, 55) is preferably conducted to the reflux of at least one liquid-vapor contacting device, such as at least one distillation and/or fractionation column. The connection for recycling a fraction of a condensed liquid-phase effluent stream (53') from the condensation system (50) to the separation system (40) preferably terminates proximal to the top end (43) of the at least one liquid-vapor contacting device (41).

The at least one liquid-vapor contacting device (51) preferably comprises a liquid distributor (not shown) for distributing a condensed liquid-phase effluent stream (53) within the at least one liquid-vapor contacting device (51). The liquid distributor is preferably located proximal to the location of the point(s) at which the recycle stream (53) is introduced into the at least one liquid-vapor contacting device (51) and is preferably an integral part of the liquid-vapor contacting device (51).

The first cooling device (51) is preferably connected to the separation device (41) via a first reservoir (52) for accumulating condensed liquid-phase produced by the first cooling device (51). The first reservoir (52) is preferably connected to the at least one liquid-vapor contacting device (41) of the separation device (40) for conducting a recycle stream (54, 55) from the first reservoir (52) to the at least one liquid-vapor contacting device (41) of separation device (40) as a substitute for a condensed liquid-phase recycle stream (53) conducted directly from the first cooling device (51) to the separation device (40).

The first reservoir (52) provides a means for decoupling the flow rate of the recycle stream (54, 55) from the flow rate of the condensate effluent stream (53) produced by the at least one cooling device (51). Decoupling may be used to reduce or eliminate flow rate variations in recycle stream (54, 55), so that recycle stream (54, 55) may be introduced into separation device (40) at a relatively constant rate in comparison to the flow rate of the condensed liquid-phase effluent stream (53). The first reservoir may also function as a liquid-vapor separator for enhancing separation of the liquid and vapors resulting from the first cooling device.

The fraction of the condensed liquid-phase effluent stream (53) in excess of the fraction of the condensed liquid-phase effluent stream (53) recycled to separation device (40) is conducted as first product stream (54,56) from the first condensation system (50) to a storage vessel, another reservoir, or a reaction vessel for further processing. In one embodiment, the first product stream (54, 56) is conducted directly, or indirectly, to a dehydrochlorination reaction vessel suitable for converting DCH to epichlorohydrin. The dehydrochlorination reaction vessel is preferably suitable for contacting DCH with a base, such as an alkali metal, or alkaline earth metal, base, such as sodium hydroxide or calcium hydroxide or carbonate, respectively, in the presence of water, which is preferably in the liquid state.

A second condensation system generally indicated by numeral (60) is connected to the first condensation system (50) for conducting the vapor-phase effluent stream (57) from first condensation system (50) to the second condensation system (60) to form a second condensed liquid-phase product stream (61).

The second condensation system (60) comprises a second cooling device (61) and, optionally, a second reservoir (62) connected to the second cooling device (61) for accumulation of condensate from the second cooling device (61). The second reservoir may also function as a liquid-vapor separator for enhancing separation of the liquid and the vapors resulting from the second cooling device.

The second cooling device (61) is suitable for cooling the vapor phase effluent stream (57) to a third temperature, which is lower than the second temperature of second vapor-phase effluent stream, and preferably lower than the dewpoint of water, at the operating pressure of the second condensation system (60). The second cooling device (61) is preferably a nonadiabatic cooling device.

The second cooling device (61) is preferably one or more condensers. The condensers preferably comprise one or more coolant passages made of heat-conductive material for conducting a fluid cooling medium, such as an aqueous or glycolic liquid phase, having a temperature at or below the above-mentioned third temperature. The optional second reservoir (62) is preferably adapted to receive condensate from one or more condensers of cooling device (61).

In one optional embodiment, the second cooling device (61) is connected to the first cooling device (51) for conducting a fluid cooling medium, such as water, from the second cooling device (61) to the first cooling device (51), so that the fluid cooling medium heated by the second nonadiabatic cooling device (61) is used as the fluid cooling medium in the first cooling device (51) to reduce the demand for cooling medium.

The second condensed liquid-phase product stream (63) is conducted as second product stream (63) from the second cooling device (61) to a storage vessel, another reservoir, or a reaction vessel for further processing. In one embodiment, the second condensed liquid-phase product stream (63) is conducted directly, or indirectly, to a dehydrochlorination reaction vessel suitable for converting DCH to epichlorohydrin. The dehydrochlorination reaction vessel is preferably suitable for contacting DCH with a base, such as an alkali metal hydroxide (e.g., sodium hydroxide) or alkaline earth metal hydroxide or carbonate (e.g., calcium hydroxide), in the presence of water, which is preferably in the liquid state The dehydrochlorination reaction vessel may be, and preferably is, the same dehydrochlorination reaction vessel as the dehydrochlorination reaction vessel that may be connected to the first condensation system (50) via the first liquid-phase product stream (54, 56).

The second cooling device (61) is preferably connected to a second reservoir (62) for conducting the second condensed liquid-phase product stream (63) from the second cooling device (61) to the second reservoir (62). The second reservoir (62) provides a means for decoupling the flow rate of the second liquid-phase product stream (65) from flow rate variations in second condensed liquid-phase effluent stream (63) for introducing the second condensed liquid-phase product stream (65) into the next unit operation, such as a reactor, at a controlled or constant rate in comparison to the flow rate of the condensed liquid-phase effluent stream (63) in a manner analogous to the function of the first reservoir (52).

The third vapor phase effluent stream (64) may be conducted from the second cooling device (61) to another unit operation, such as a liquid-vapor contacting device (e.g., a scrubber) for removing and/or recycling chlorinating agent, such as hydrogen chloride gas and/or hydrochloric acid.

Figure 2:
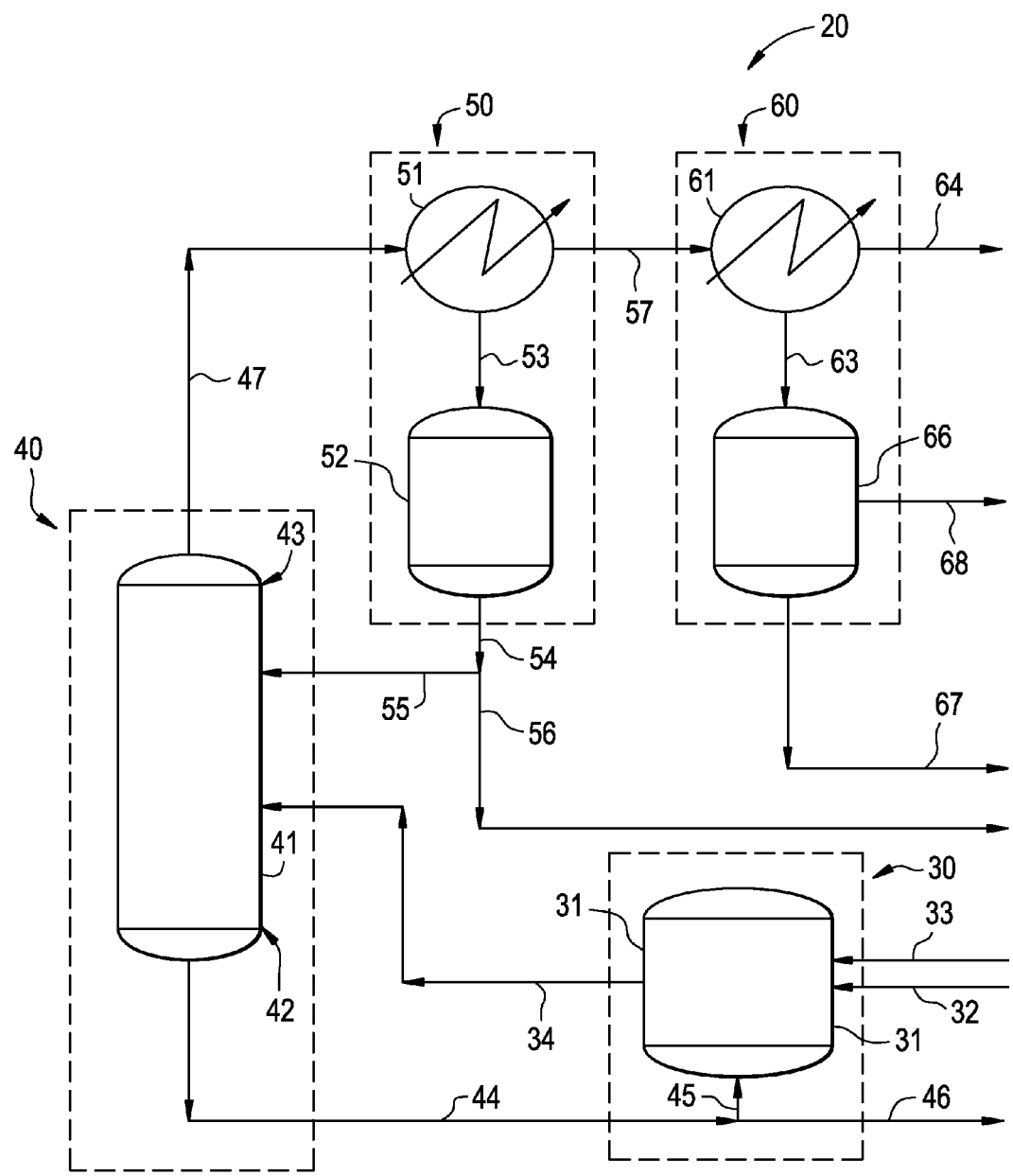
FIG. 2 is a process diagram illustrating a second embodiment of the present invention.

A second embodiment of an apparatus of the invention for producing DCH is shown in FIG. 2, and generally indicated by numeral (20). The embodiment of the apparatus shown in FIG. 2 is the same as in FIG. 1 except that in the apparatus (20), the second condensation system (60) is connected to a liquid-liquid phase separator (66). The liquid-liquid phase separator (66) separates a liquid aqueous phase (68) from a liquid organic phase (67). The liquid-liquid phase separator (66) may, for example, be a decanter.

The liquid organic phase effluent stream (67) from the liquid-liquid phase separator (66) may be stored or conducted to another unit operation, such as a dehydrochlorination reactor, and/or combined with liquid-phase product stream (56) for storage or further processing as previously described above for liquid-phase product stream (56).

The liquid aqueous phase effluent stream (68) from the liquid-liquid phase separator (66) may be used in a downstream dehydrochlorination reactor to recover and convert DCH(s) remaining in the separated aqueous phase and to provide process water to the above-mentioned dehydrochlorination reactor for maintaining chloride salts, such as alkali metal chloride salt(s) or alkaline earth metal chloride salt(s), produced by reacting DCH with an alkali metal or alkaline earth metal base, below their saturation limit in the liquid to keep the salts from precipitating.

The remainder of FIG. 2, including the definitions of apparatus components and streams, is substantially the same as in FIG. 1.

In each of FIGS. 1 and 2, vapor-phase stream (64) is preferably connected, directly or indirectly, to a downstream vacuum generating device (not shown) for reducing the pressure of the vapor phase within the apparatus below atmospheric pressure. The vacuum generating device is preferably downstream of the optional unit operation for removing chlorinating agent, such as the liquid-vapor contacting device used as a scrubber described above. The vacuum-generating device is preferably a vacuum pump or steam ejector.

To the extent that components of the above apparatus are exposed to corrosive materials, such components are preferably fabricated of materials which are resistant to corrosion by the process components. *Kirk-Othmer Encyclopedia of Chemical Technology*, $2^{nd}$ Edition (John Wiley and Sons, 1966), volume 11, pages 323-327, presents an extensive discussion of the corrosion resistance of metals and non-metals that can be used in hydrochloric acid and hydrogen chloride service. Specific examples of suitable materials are disclosed in WO 2006/020234. Specific examples include metals such as tantalum, suitable metallic alloys (particularly nickel-molybdenum alloys such as Hastalloy C©), or glass-lined, plastic-lined or graphite equipment.

The following examples are for illustrative purposes only and are not intended to limit the scope of the present invention.

Equipment Used in the Examples

EXAMPLE 1

Distillation is carried out using a glass distillation column packed with 6 mm ceramic Intalox saddles containing two packed bed sections. Feed to the column is located between the two packed bed sections. The column is provided with a glass reboiler and two partial condensers in series, also made of glass, for cooling the vapor stream exiting the column. The first condenser is located directly on top of the column and was cooled with chilled glycol. A portion of the condensate from the first condenser is returned to the column as reflux and the rest of the condensate is collected as product.

Uncondensed vapors from the first condenser are condensed in the second condenser operating at a lower temperature and cooled with chilled glycol. The uncondensed vapors exiting the second condenser are passed through a set of cold traps before entering the vacuum pump which provides vacuum to the whole system. The second condensed liquid-phase effluent from the second condenser enters a liquid-liquid separator. Under the process conditions used in this example, only a small amount of liquid organic phase is occasionally separated from the substantially aqueous second condensed liquid-phase effluent.

In this example, a DCH recovery process is conducted according to the present invention based on the distillation column process conditions shown in Table 1 below:

TABLE 1

| Distillation Column Process Conditions | | Units |
| --- | --- | --- |
| Pressure at the top of the column | 1.6 | kPa |
| Temperature at the top of the column | 50 | ° C. |
| First condenser temperature | 15 | ° C. |
| Second condenser temperature | 0 | ° C. |
| Fraction of 1$^{st}$ condenser product recycled to the column for reflux | 0.25 | |

The distillation data is shown in Table 2.

TABLE 2

| Subject | Feed | First condenser product 2$^{nd}$ fraction | Second condenser product | Vent | Bottoms | Units |
| --- | --- | --- | --- | --- | --- | --- |
| Fraction of feed to the column | 1 | 0.39 | 0.01 | balance | 0.59 | |
| H$_2$O | 8.9 | 20.1 | 56.6 | | — | wt. % |
| HCl | 3.3 | 7.2 | 21.9 | | — | wt. % |
| 1,3-dichloro-2-propanol | 33.1 | 70.8 | 21.1 | | 7.4 | wt. % |
| 2,3-dichloro-1-propanol | 7.1 | 1.8 | 0.3 | | 11.0 | wt. % |
| other components | 47.6 | — | — | | 81.6 | wt. % |

In Table 2 alone and its subsequest tables,

"Feed" refers to stream (34) in FIG. 1;

"First condenser product" refers to stream (56) in FIG. 1;

"Second condenser product" refers to stream (63) in FIG. 1;

"Vent" refers to the third vapor phase stream (64) in FIG. 1;

"Bottoms" refers to the distillation residue stream (44) of FIG. 1; and a hyphen ("—") indicates that the weight-percent value is below 0.01.

Table 2 above shows that the feed stream to the distillation column comprising dichlorohydrins is separated into a top product stream comprising primarily dichlorohydrins and a bottom product stream comprising the heavier components in the feed stream such as MCH, glycerol and other components including the catalyst and its esters, ethers and higher molecular weight compounds, often called heavies. The first product stream from the first condenser contains primarily DCHs as shown in the example above whereas the second product stream from the second condenser is a water-rich aqueous stream. The measurements provided in Table 2 above are within experimental measurement error of about +/−3 percent relative error.

EXAMPLE 2

Distillation is carried out, using a glass lined distillation column packed with graphite packing, containing two packed bed sections. Feed to the column is located between the two packed bed sections. The column is provided with a reboiler and two partial condensers in series, made of graphite, for cooling the vapor stream exiting the column. The first condenser is cooled with cooling water. A portion of the condensate from the first condenser is returned to the column as reflux and the rest of the condensate is collected as product.

Uncondensed vapors from the first condenser are condensed in the second condenser operating at a lower temperature and cooled with chilled glycol. The uncondensed vapors exiting the second condenser are passed to the steam ejector vacuum pump which provides vacuum to the whole system. The second condensed liquid-phase effluent from the second condenser is collected in an intermediate vessel as product. The measurements provided in Table 2 above are within experimental measurement error of about +/−5 percent relative error.

Table 3 below provides some of the key operating conditions in the equipment:

TABLE 3

| Distillation Column Process Conditions | | Units |
| --- | --- | --- |
| Pressure at the top of the column | 4.5 | kPa |
| Temperature at the top of the column | 67 | ° C. |
| First condenser temperature | 45 | ° C. |

TABLE 3-continued

| Distillation Column Process Conditions | | Units |
| --- | --- | --- |
| Second condenser temperature | 10 | ° C. |
| Fraction of 1$^{st}$ condenser product recycled to the column for reflux | 0.5 | |

The distillation data is shown in Table 4.

TABLE 4

| Subject | Feed | First condenser product - 2$^{nd}$ fraction | Second condenser product | Vent | Bottoms | Units |
|---|---|---|---|---|---|---|
| Fraction of feed to the column | 1 | 0.17 | 0.16 | balance | 0.63 | |
| H$_2$O | 6.2 | 2.8 | 40.7 | — | — | wt. % |
| HCl | 2.5 | 1.3 | 12.5 | — | — | wt. % |
| 1,3-dichloro-2-propanol | 34.9 | 90.4 | 44.9 | — | 16.9 | wt. % |
| 2,3-dichloro-1-propanol | 7.6 | 5.5 | 1.9 | — | 9.4 | wt. % |
| other components | 48.8 | — | — | — | 73.7 | wt. % |

Table 4 above shows that the feed stream to the distillation column comprising dichlorohydrins is separated into a top product stream comprising primarily dichlorohydrins and a bottom product stream comprising the heavier components in the feed stream such as MCHs, glycerol and other components which include the catalyst and its esters, ethers and higher molecular weight compounds, often called heavies. The first product stream from the first condenser contains greater than 95 weight percent DCHs as shown in the example above whereas the second product stream from the second condenser contains high concentrations of both DCHs and water.

EXAMPLE 3

This example is based on a computer simulation of the process using commercially available software and physical properties and thermodynamic models of the major components. Table 5 provides key process conditions in the equipment and Table 6 provides mass flow rates and compositions for the feed and the product streams.

TABLE 5

| Distillation Column Process Conditions | | Units |
|---|---|---|
| Pressure at the top of the column | 4.5 | kPa |
| Temperature at the top of the column | 68 | ° C. |
| First condenser temperature | 45 | ° C. |
| Second condenser temperature | 10 | ° C. |
| Fraction of 1$^{st}$ condenser product recycled to the column for reflux | 0.43 | |

The computer model-generated distillation results are shown in Table 6.

TABLE 6

| Subject | Feed | First condenser product - 2$^{nd}$ fraction | Second condenser product | Vent | Bottoms | Units |
|---|---|---|---|---|---|---|
| Fraction of feed to the column | 1 | 0.15 | 0.18 | balance | 0.67 | |
| H$_2$O | 7.0 | 0.75 | 38.7 | — | — | wt. % |
| HCl | 3.0 | — | 16.9 | — | — | wt. % |
| 1,3-dichloro-2-propanol | 33.2 | 96.4 | 43.4 | — | 17.2 | wt. % |
| 2,3-dichloro-1-propanol | 1.4 | 2.8 | 1.0 | — | 1.3 | wt. % |
| other components | 55.4 | — | — | — | 81.5 | wt. % |

The results shown in Table 6 (from a computer simulation) are similar to the results shown in Table 4 from an experiment. The first product stream from the first condenser in Table 6 contains greater than 99 weight percent dichlorohydrins.

What is claimed is:

1. An apparatus suitable for producing dichlorohydrin(s) from multihydroxylated-aliphatic hydrocarbon compound(s) and/or ester(s) thereof comprising:

(1) a reactor system suitable for carrying out hydrochlorination of multi-hydroxylated aliphatic hydrocarbon compound(s) and/or ester(s) thereof comprising one or more reactors connected in series or in parallel;

(2) a separation system comprising a liquid-vapor contacting device having a source of heat at the bottom end of the liquid-vapor contacting device; wherein the liquid-vapor contacting device is suitable for distillation of a reactor effluent stream obtainable from the reactor system; and, optionally, at least one flash vessel;

(3) a first condensation system comprising a first cooling device and optionally a first reservoir connected to the cooling device for accumulation of condensate from the first cooling device;

(4) a second condensation system comprising a second cooling device and optionally (a) a second reservoir connected to the second cooling device for accumulation of condensate from the second cooling device or (b) a liquid-liquid phase separation device connected to the second cooling device for separating a liquid phase comprising aqueous and organic components into an aqueous phase and an organic phase separate from the aqueous phase; and (5) a means for applying a vacuum, directly or indirectly, to the liquid-vapor contacting device for reducing the pressure in the liquid-vapor contacting device below atmospheric pressure; and wherein the means for applying a vacuum is located downstream from the second condensation system;

wherein the at least one reactor system is connected to the separation system for conducting a reactor effluent stream from the reactor system to the separation system for distillation and/or fractionation of the reactor efflu-ent stream; the separation system is connected to the first condensation system for conducting a first vapor-phase distillation and/or fractionation effluent stream from the separation system to the first condensation system; the first condensation system is connected to the second condensation system for conducting a second vapor-phase effluent stream from the first condensation system to the second condensation system; and the first condensation system is connected to the separation system for conducting a fraction of a first condensed liquid-phase effluent stream from the first condensation system to the separation system.

2. The apparatus according to claim 1, wherein the first cooling device of the first condensation system is located on top of the liquid-vapor contacting device of the separation device; or wherein the first cooling device is an integral part of the liquid-vapor contacting device.

3. The apparatus according to claim 1, wherein the liquid-vapor contacting device is a packed distillation column; or wherein the liquid-vapor contacting device is a distillation column adapted for carrying out fractional distillation under reflux conditions.

4. The apparatus according to claim 1, wherein the liquid-vapor contacting device is connected to the reactor system for conducting a recycle stream from the bottom end of the liquid-vapor contacting device to the reactor system.

5. The apparatus according to claim 1, wherein the one or more reactors of the reactor system comprises a plug flow reactor.

6. An apparatus suitable for producing dichlorohydrin(s) from multihydroxylated-aliphatic hydrocarbon compound(s) and/or ester(s) thereof comprising:
   (1) a reactor system suitable for carrying out hydrochlorination of multi-hydroxylated aliphatic hydrocarbon compound(s) and/or ester(s) thereof comprising one or more reactors connected in series or in parallel;
   (2) a separation system comprising a liquid-vapor contacting device having a source of heat at the bottom end of the liquid-vapor contacting device; wherein the liquid-vapor contacting device is suitable for distillation of a reactor effluent stream obtainable from the reactor system; and, optionally, at least one flash vessel;
   (3) a first condensation system comprising a first cooling device and optionally a first reservoir connected to the cooling device for accumulation of condensate from the first cooling device; and
   (4) a second condensation system comprising a second cooling device and optionally (a) a second reservoir connected to the second cooling device for accumulation of condensate from the second cooling device or (b) a liquid-liquid phase separation device connected to the second cooling device for separating a liquid phase comprising aqueous and organic components into an aqueous phase and an organic phase separate from the aqueous phase;
   wherein the at least one reactor system is connected to the separation system for conducting a reactor effluent stream from the reactor system to the separation system for distillation and/or fractionation of the reactor effluent stream; the separation system is connected to the first condensation system for conducting a first vapor-phase distillation and/or fractionation effluent stream from the separation system to the first condensation system; the first condensation system is connected to the second condensation system for conducting a second vapor-phase effluent stream from the first condensation system to the second condensation system; and the first condensation system is connected to the separation system for conducting a fraction of a first condensed liquid-phase effluent stream from the first condensation system to the separation system;
   wherein the liquid-vapor contacting device is a packed distillation column; or wherein the liquid-vapor contacting device is a distillation column adapted for carrying out fractional distillation under reflux conditions;
   wherein the first condensation system is connected to a second reactor suitable for conducting dehydrochlorination for conducting a first condensed liquid-phase effluent stream from the first condensation system to the second reactor; wherein the second condensation system is connected to the second reactor suitable for conducting dehydrochlorination for conducting a second condensed liquid-phase effluent stream from the second condensation system to the second reactor; wherein the second condensation system comprises a liquid-liquid phase separation device for separating a liquid aqueous phase from a liquid organic phase and the second cooling device of the second condensation system is connected to the liquid-liquid phase separation device for conducting a condensed liquid-phase from the second cooling device to the liquid-liquid phase separation device; and wherein the liquid-liquid phase separation device, is connected to the second reactor suitable for conducting dehydrochlorination for conducting an organic liquid-phase effluent stream and/or an aqueous liquid phase effluent stream from the liquid-liquid phase separation device to the second reactor.

* * * * *